(12) United States Patent
Lee et al.

(10) Patent No.: US 11,992,683 B2
(45) Date of Patent: May 28, 2024

(54) BIOIMPEDANCE MEASUREMENT METHOD AND APPARATUS WITH ELECTRICAL STIMULATION PERFORMANCE

(71) Applicant: Samsung Electronics Co., Ltd., Suwon-si (KR)

(72) Inventors: Hyungwoo Lee, Seoul (KR); Sang Joon Kim, Hwaseong-si (KR); Jongpal Kim, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

(21) Appl. No.: 18/118,376

(22) Filed: Mar. 7, 2023

(65) Prior Publication Data

US 2023/0218902 A1 Jul. 13, 2023

Related U.S. Application Data

(62) Division of application No. 16/655,596, filed on Oct. 17, 2019, now Pat. No. 11,623,094.

(30) Foreign Application Priority Data

Dec. 14, 2018 (KR) .................. 10-2018-0162168
Sep. 3, 2019 (KR) .................. 10-2019-0108798

(51) Int. Cl.
*A61N 1/24* (2006.01)
*A61B 5/0536* (2021.01)
(Continued)

(52) U.S. Cl.
CPC ........ *A61N 1/36125* (2013.01); *A61B 5/0536* (2013.01); *A61B 5/24* (2021.01)

(58) Field of Classification Search
CPC ............ A61N 1/36125; A61N 1/36014; A61N 1/3603; A61N 1/36; A61N 1/36002;
(Continued)

(56) References Cited

U.S. PATENT DOCUMENTS 9,220,895 B2 12/2015 Siff et al.
2006/0149337 A1* 7/2006 John .................. A61N 1/36064
607/45

(Continued)

FOREIGN PATENT DOCUMENTS

KR 10-2015-0028996 A 3/2015
KR 10-1747029 B1 6/2017
(Continued)

OTHER PUBLICATIONS

Product Pamphlet, "Drager Pulmo Vista 500", Drägerwerk AG & Co. KgaA (5 pages in English and 6 pages in Korean).
(Continued)

*Primary Examiner* — Carl H Layno
*Assistant Examiner* — Anh-Khoa N Dinh
(74) *Attorney, Agent, or Firm* — NSIP Law

(57) ABSTRACT

Aspects of the subject disclosure may include, for example, a method and apparatus for measuring a bioimpedance and performing an electrical stimulation, the method including generating a first current corresponding to a first high-frequency, generating a second current corresponding to a second high-frequency, generating a low-frequency current based on a beat phenomenon of the first current and the second current, and calculating an impedance of a target part based on a voltage induced to the target part by a high-frequency current corresponding to at least one of the first current and the second current and the low-frequency current.

10 Claims, 9 Drawing Sheets

(51) Int. Cl.
*A61B 5/24* (2021.01)
*A61N 1/36* (2006.01)

(58) Field of Classification Search
CPC ............ A61N 1/36003; A61N 1/36007; A61N 1/36036; A61N 1/3604; A61N 1/36042; A61N 1/36046; A61N 1/3605; A61N 1/36053; A61N 1/36057; A61N 1/3606; A61N 1/18; A61N 1/20; A61N 1/32; A61B 5/0536; A61B 5/24; A61B 5/4041; A61B 5/053
See application file for complete search history.

(56) References Cited

U.S. PATENT DOCUMENTS

| | | |
|---|---|---|
| 2010/0152817 A1 | 6/2010 | Gillbe |
| 2015/0137831 A1* | 5/2015 | Pluta .................... G01R 33/323 324/647 |
| 2015/0342497 A1 | 12/2015 | Maktura et al. |
| 2015/0360027 A1 | 12/2015 | Bachinski et al. |
| 2017/0182324 A1 | 6/2017 | Carroll |
| 2018/0092560 A1 | 4/2018 | Holder et al. |

FOREIGN PATENT DOCUMENTS

| | | |
|---|---|---|
| WO | WO 2014/029631 A1 | 2/2014 |
| WO | WO 2015/083958 A1 | 6/2015 |
| WO | WO 2016/170327 A1 | 10/2016 |

OTHER PUBLICATIONS

Hong, Sunjoo et al., "A 4.9 mΩ-Sensitivity Mobile Electrical Impedance Tomography IC for Early Breast-Cancer Detection System", *IEEE Journal of Solid-State Circuits*, vol. 50, No. 1, Jan. 2015 (pp. 245-257).

Hong Sunjoo et al., "A 10.4 mW Electrical Impedance Tomography SoC for Portable Real-Time Lung Ventilation Monitoring System", *IEEE Journal of Solid-State Circuits*, vol. 50, No. 11, Nov. 2015 (pp. 2501-2512).

Seo, Jin Keun et al, "Frequency-difference electrical impedance tomography (fdEIT): algorithm development and feasibility study", *Physiol. Meas.* vol. 29, 2008 (pp. 929-944).

Extended European Search Report dated Feb. 13, 2020 in corresponding European Application No. 19214087.9 (15 pages in English).

* cited by examiner

BIOIMPEDANCE MEASUREMENT METHOD AND APPARATUS WITH ELECTRICAL STIMULATION PERFORMANCE

CROSS-REFERENCE TO RELATED APPLICATIONS

This application is a division of U.S. patent application Ser. No. 16/655,596, filed on Oct. 17, 2019, now U.S. Pat. No. 11,623,094 B2, which claims the benefit under 35 USC 119(a) of Korean Patent Application No. 10-2018-0162168 filed on Dec. 14, 2018, and Korean Patent Application No. 10-2019-0108798 filed on Sep. 3, 2019, in the Korean Intellectual Property Office, the entire disclosure of which is incorporated herein by reference for all purposes.

BACKGROUND

1. Field

The following description relates to a bioimpedance measurement method and apparatus with electrical stimulation performance.

2. Description of Related Art

A bioimpedance or bioelectrical impedance of a body part such as the brain, heart, stomach, muscles, and nerves may be used to detect a state of the body part, and a phenomenon or mechanism occurring in the body part. Additionally, through the application of an electrical stimulation, an action for purposes of treatment, rehabilitation, beauty, and the like may be taken on the body part. For example, an electrical impedance tomography (EIT) refers to technology that allows a visual analysis of a difference of impedance changing with time or frequency by measuring the difference of impedance through multiple channels and imaging measured data. The EIT technology monitors a difference in impedance changing with time or frequency. The monitoring of a difference in impedance changing with time is referred to as a time difference (TD) ETI, and the monitoring of a difference of impedance changing with frequency is referred to as a frequency difference (FD) ETI.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a general aspect, an impedance measuring apparatus includes a first high-frequency current generator configured to generate a first current corresponding to a first high-frequency, a second high-frequency current generator configured to generate a second current corresponding to a second high-frequency, a low-frequency current generator configured to generate a low-frequency current based on a beat phenomenon of the first current and the second current, and a controller configured to calculate an impedance of a target part based on a voltage induced to the target part by a high-frequency current corresponding to at least one of the first current and the second current, and the low-frequency current.

The biopotential measurer may be configured to measure a voltage applied to the target part based on the high-frequency current and the low-frequency current.

The apparatus may include an electrode array comprising a plurality of electrodes configured to contact the target part, and an electrode switching network configured to selectively connect at least one of the first high-frequency current generator, the second high-frequency current generator, and the low-frequency current generator to at least one of the plurality of electrodes.

The target part may correspond to a nerve bundle, and the plurality of electrodes are arranged to surround the nerve bundle.

The low-frequency current generator may be configured to generate the low-frequency current based on an envelope of a combined current of the first current and the second current.

The low-frequency current may have a low-frequency corresponding to a difference between the first high-frequency and the second high-frequency.

The apparatus may further include an electrode array comprising a plurality of electrodes configured to contact the target part, wherein when a stimulation area is selected in the target part, the controller is configured to select one or more electrodes corresponding to the stimulation area from the plurality of electrodes.

When the first current and the second current are applied to the selected one or more electrodes, the first current and the second current may overlap in the stimulation area to induce a low-frequency electrical stimulus to the stimulation area based on a beat phenomenon.

The target part may correspond to a nerve bundle and the stimulation area corresponds to at least one nerve in the nerve bundle.

In a general aspect, an impedance measurement method includes generating a first current corresponding to a first high-frequency, generating a second current corresponding to a second high-frequency, generating a low-frequency current based on a beat phenomenon of the first current and the second current, and calculating an impedance of a target part based on a voltage induced to the target part by a high-frequency current corresponding to at least one of the first current and the second current, and the low-frequency current. In a general aspect, an electronic device includes a plurality of electrodes configured to contact a body part, a first high-frequency current generator configured to generate a first high-frequency current, a second high-frequency current generator configured to generate a second high-frequency current, a low-frequency current generator configured to receive the first high-frequency current and the second high-frequency current and generate a current of a low-frequency corresponding to a difference between a first high-frequency of the first high-frequency current and a second high-frequency of the second high-frequency current, and a controller configured to select electrodes to which the first high-frequency current and the second high-frequency current are to be applied, from among the plurality of electrodes.

The first high-frequency and the second high-frequency may range from 20 to 200 kilohertz (KHz), and the low-frequency may range from 5 to 30 hertz (Hz). The total volume of the first high-frequency current generator, the second high-frequency current generator, and the low-frequency current generator may be less than 1 cubic centimeter ($cm^3$). The first high-frequency current generator and the second high-frequency current generator may be configured as a chip, and the area of the chip may be less than 25 square millimeters (mm²).

A mode in which the controller applies the first high-frequency current and the second high-frequency current to the selected electrodes may be a stimulation mode, and the controller may have a measurement mode for applying the low-frequency current.

Other features and aspects will be apparent from the following detailed description, the drawings, and the claims.

Figure 1:
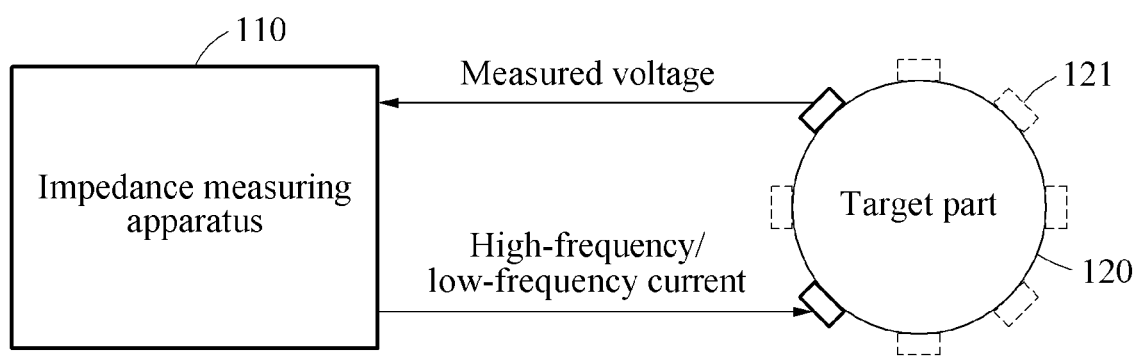
FIG. 1 illustrates an example of an impedance measuring apparatus and a target part, in accordance with one or more embodiments.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Unless otherwise defined, all terms, including technical and scientific terms, used herein have the same meaning as commonly understood by one of ordinary skill in the art to which this disclosure pertains after an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

FIG. 1 illustrates an example of an impedance measuring apparatus and a target part.

Referring to FIG. 1, an impedance measuring apparatus 110 may apply a high-frequency current and a low-frequency current to a target part 120 and measure a voltage of the target part 120. The impedance measuring apparatus 110 may measure an impedance of the target part 120 based on a current applied to the target part 120 and a voltage applied to the target part 120 in a state in which the current is applied to the target part 120. For example, the target part 120 may correspond to body parts such as cells, tissues, nerves, a nerve bundle, and an organ of a living body, but is not limited thereto. The impedance of the target part 120 includes a bioimpedance of the target part 120. Herein, it is noted that use of the term 'may' with respect to an example or embodiment, e.g., as to what an example or embodiment may include or implement, means that at least one example or embodiment exists where such a feature is included or implemented while all examples and embodiments are not limited thereto.

The impedance measuring apparatus 110 applies the current to the target part 120 using an electrode array including at least one electrode 121, and measures the voltage applied to the target part 120. Electrodes in the electrode array may be arranged to surround the target part 120. The impedance measuring apparatus 110 may select a first set of electrodes from the plurality of electrodes, and applies the current to the target part 120 using the selected first set of electrodes. Additionally, the impedance measuring apparatus 110 may select a second set of electrodes from the remaining electrodes and measure the voltage from the target part 120 using the selected second set of electrodes. Hereinafter, for ease of description, an electrode that applies a current is referred to as a current electrode and an electrode that measures a voltage is referred to as a voltage electrode. The impedance measuring apparatus 110 measures the impedance of the target part 120 through a rotation of the current electrode and the voltage electrode.

The impedance measuring apparatus 110 measures the impedance of the target part 120 based on an electrical impedance tomography (EIT). The EIT refers to technology for monitoring a difference of an impedance changing with time or frequency through multiple channels and imaging measured data so that the difference of the impedance is visually analyzed. The impedance measuring apparatus 110 surrounds a tissue to be measured with an electrode array, flows a sine-wave current, for example, a current stimulator in a predetermined interval, measures a voltage through multiple channels by turns, and measures an impedance for each section. Impedance values measured based on an electrode rotation are converted into images. When the images acquired through such processes are consecutively displayed according to time, a difference in tissue corresponding to a difference in impedance may be visually confirmed.

The EIT technology monitors a difference in impedance changing with time or frequency. A scheme of monitoring a difference of impedance changing with time is referred to as a time difference (TD) ETI, and a scheme of monitoring a difference in impedance changing with frequency is referred to as a frequency difference (FD) ETI. For example, the TD ETI may be used to observe a difference of impedance changing with time. Additionally, the FD ETI may be performed when at least two different tissues are present in a monitoring target part and the tissues are to be visually differentiated and monitored based on a difference in a rate of change of impedance based on a frequency.

In an example, the TD ETI may be used to monitor a difference that occurs in the size of lungs when the size of the lungs changes due to inhalation and exhalation. Additionally, in an example, when a cancer cell is in normal cells, the FD ETI may be used to visually distinguish the cancer cell from the normal cells based on a rate of change of impedance which is different for each frequency. The TD ETI and the FD ETI may be used in combination. The combination of the TD ETI and the FD ETI may increase a resolution of an image. Thus, the TD ETI and the FD ETI may be generally used in combination.

The FD ETI measures an impedance appearing at a low-frequency and an impedance appearing at a high-frequency through an electrode array in sequence, recodes an impedance difference for each position in a tissue, and images the impedance difference. Thus, in the FD ETI, a low-frequency measurement and a high-frequency measurement should be performed separately. For example, the low-frequency may be 5 to 30 hertz (Hz) and the high-frequency may be 20 to 200 k Hz. The high-frequency and the low-frequency may also be defined as other various values.

In the EIT, a sine-wave current is used to measure an impedance. For example, the sine-wave current may be generated to have a desired frequency component through a circuit including a Wein-bridge oscillator. In a case of an implantable electronic medicine system such as a brain nerve EIT to replace functional magnetic resonance imaging (fMRI) or a nerve bundle EIT to detect a neuronal active area due to behavior or stimulation, miniaturization of a product may be required.

A desired frequency may be determined using f=1/(RC Time Constant) in which RC Time Constant=2*Circular constant*R*C. If a frequency used for impedance measurement is a high-frequency, values of R and C may be small because the values of R and C are inversely proportional to the frequency. If a frequency used for impedance measurement is a low-frequency, the values of R and C may be large because the values of R and C are proportional to the frequency. For example, passive elements of 6R and 2.5C may be required to obtain a desired frequency in the Wein-bridge oscillator. When a desired frequency is 100 k Hz, R=80 k(ohm) and C=18p(F). However, when a desired frequency is 10 Hz, R=8G(ohm) and C=1.8n(F). In this example, volumes of passive elements are so large that it is difficult to realize a small-sized system.

A low-frequency signal is generated based on a beat phenomenon, whereby a size of a passive element for sine-wave generation is significantly reduced. The impedance measuring apparatus 110 combines high-frequency currents and generates a low-frequency current by detecting an envelope from the combined current. This is because, when a signal having a frequency f1 is combined with a signal having a frequency f2, an envelope of the combined signal may have a frequency of |f1−f2| due to the beat phenomenon. As such, the impedance measuring apparatus 110 generates a low-frequency current using high-frequency currents having a frequency difference corresponding to a desired low-frequency. The total volume of the high-frequency generators configured to generate such high-frequency currents is generally less than 1 cubic centimeter ($cm^3$) so as to be implanted into a human body. In detail, these high-frequency generators are implemented in a form of System on Chip (SoC), and the area of the chip may be implemented to be less than 25 square millimeters ($mm^2$).

The impedance measuring apparatus 110 applies an electrical stimulus to a stimulation area in the target part 120 using high-frequency currents. The impedance measuring apparatus 110 performs an operation for measuring an impedance of a target part in an impedance measurement mode and performs an operation for simulating a stimulation area in a selective stimulation mode. A low-frequency current may be suitable for applying a stimulus to a body part because the low-frequency current exerts a greater influence on the body part than the high-frequency current. When the high-frequency currents are applied to the target part 120, a low-frequency envelope due to the beat phenomenon may occur in a predetermined area in which the high-frequency currents overlap. The area in which the high-frequency currents overlap in the target part 120 is referred to as a stimulation area.

A database including areas in which a low-frequency electrical stimulation occurs due to electrodes to which the high-frequency currents are applied, or areas in which a low-frequency electrical stimulation occurs due to frequencies applied to the high-frequency currents and the electrodes to which the high-frequency currents are applied may be built in advance. The database stores electrodes matching stimulation areas, or stores electrodes, high-frequencies, and stimulation areas matching each other.

In an example, the database stores information indicating that an electrical stimulus is applied to a first stimulation area when high-frequency currents are applied to a first electrode pair, and an electrical stimulus is applied to a second stimulation area when high-frequency currents are applied to a second electrode pair. Additionally, the database stores information indicating that an electrical stimulus is applied to a first stimulation area when a high-frequency current of a first frequency and a high-frequency current of a second frequency are applied to the first electrode pair and an electrical stimulus is applied to the second stimulation area when the high-frequency current of the second frequency and a high-frequency current of a third frequency are applied to the second electrode pair. The impedance measuring apparatus 110 determines a stimulation area to which the electrical stimulus is applied, and determines electrodes corresponding to the determined stimulation area or electrodes and frequencies corresponding to the determined stimulation area based on the database.

The impedance measuring apparatus 110 determines a stimulation area based on an impedance measurement result. For example, the impedance measuring apparatus 110 determines an area where a stimulation is required to be the stimulation area based on the impedance measurement result. When the impedance measurement result indicates that that the stimulation is required in a first area in a nerve bundle, the impedance measuring apparatus 110 determines the first area to be the stimulation area, and selects appropriate electrodes or appropriate electrodes and frequencies such that a stimulus is applied to the first area. An electrode array and a high-frequency current generator are elements used for the impedance measurement. Since the electrical stimulation is performed using the electrode array and the high-frequency current generator, applicability of configurations for the impedance measuring apparatus 110 may be maximized.

Figure 2:
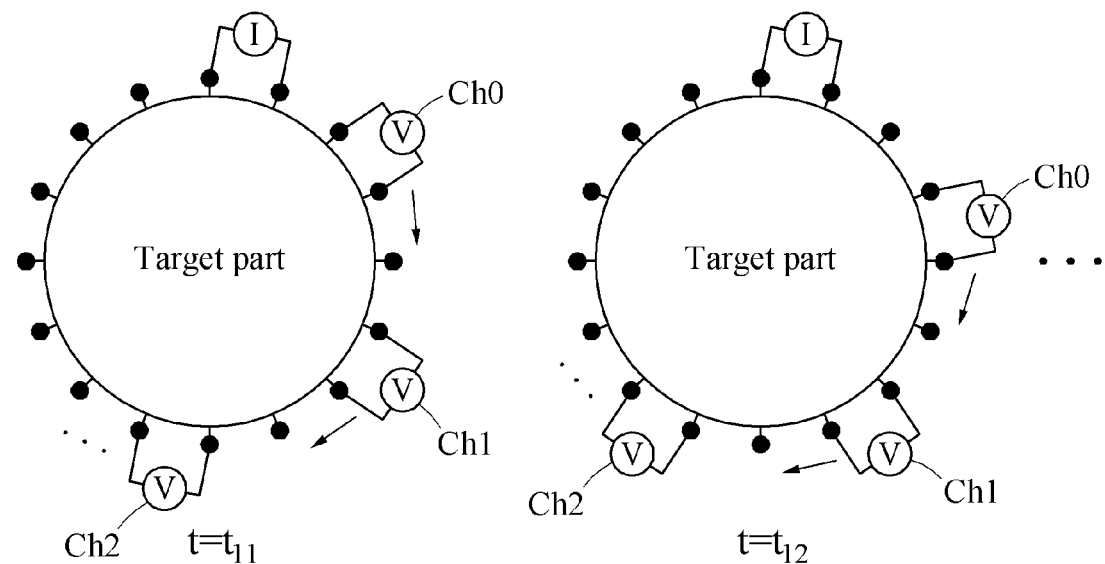
FIG. 2 illustrates an example of a rotation process for impedance measurement, in accordance with one or more embodiments.
Figure 2:
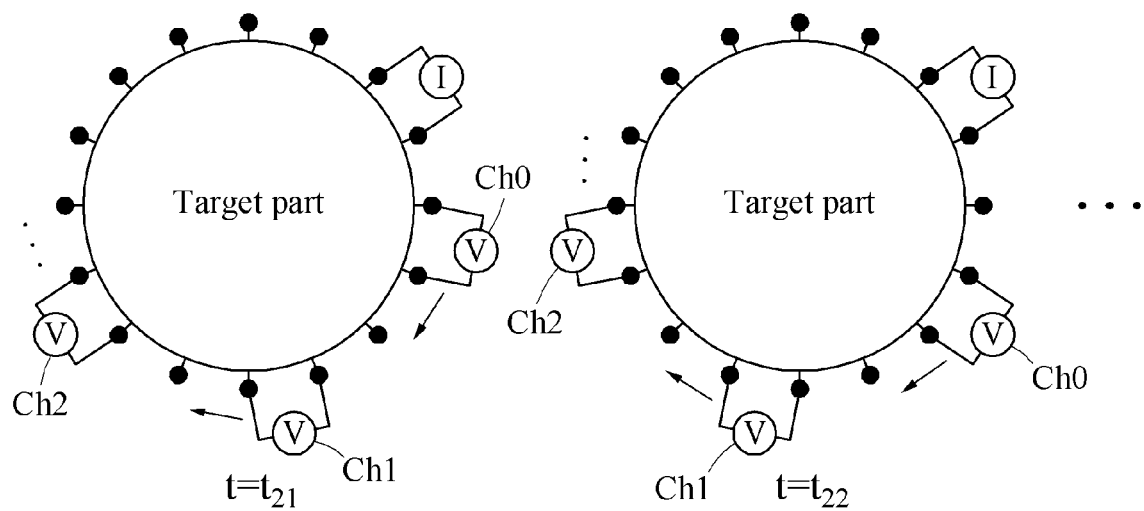

FIG. 2 illustrates an example of a rotation process for impedance measurement in accordance with one or more embodiments.

FIG. 2 illustrates a current generator I and a biopotential measurer V arranged based on a time t. Electrodes of an electrode array are arranged to surround a target part. To measure an impedance of the target part, the current generator I and the biopotential measurer V are connected by changing the electrodes. The current generator I and the biopotential measurer V are connected to all possible combinations of electrode pairs in rotation.

For example, when a current electrode is selected, a rotation for voltage electrodes may be conducted while the current electrode is fixed. When the rotation for the voltage electrodes is terminated, the current electrode is changed to another current electrode so that the rotation for the voltage electrodes is conducted while the other current electrode is fixed. When a rotation for current electrodes is terminated through such process, an impedance of the target part is calculated based on voltage values collected during the process. The calculated impedance may be imaged and provided to a user.

In the example of FIG. 2, $t=t_{ij}$, i being a current electrode and j being a voltage electrode. When $t=t_{1j}$, a voltage electrode is changed in a state in which a current electrode corresponding to i=1. Also, when $t=t_{2j}$, the voltage electrode is changed to another voltage electrode in a state in which a current electrode corresponding to i=2. A voltage of the target part may be measured based on multiple channels. FIG. 2 illustrates a three-channel measurement process of Ch0 through Ch2. Depending on an example, a number of channels for voltage measurement may be selected in various ways.

Figure 3:
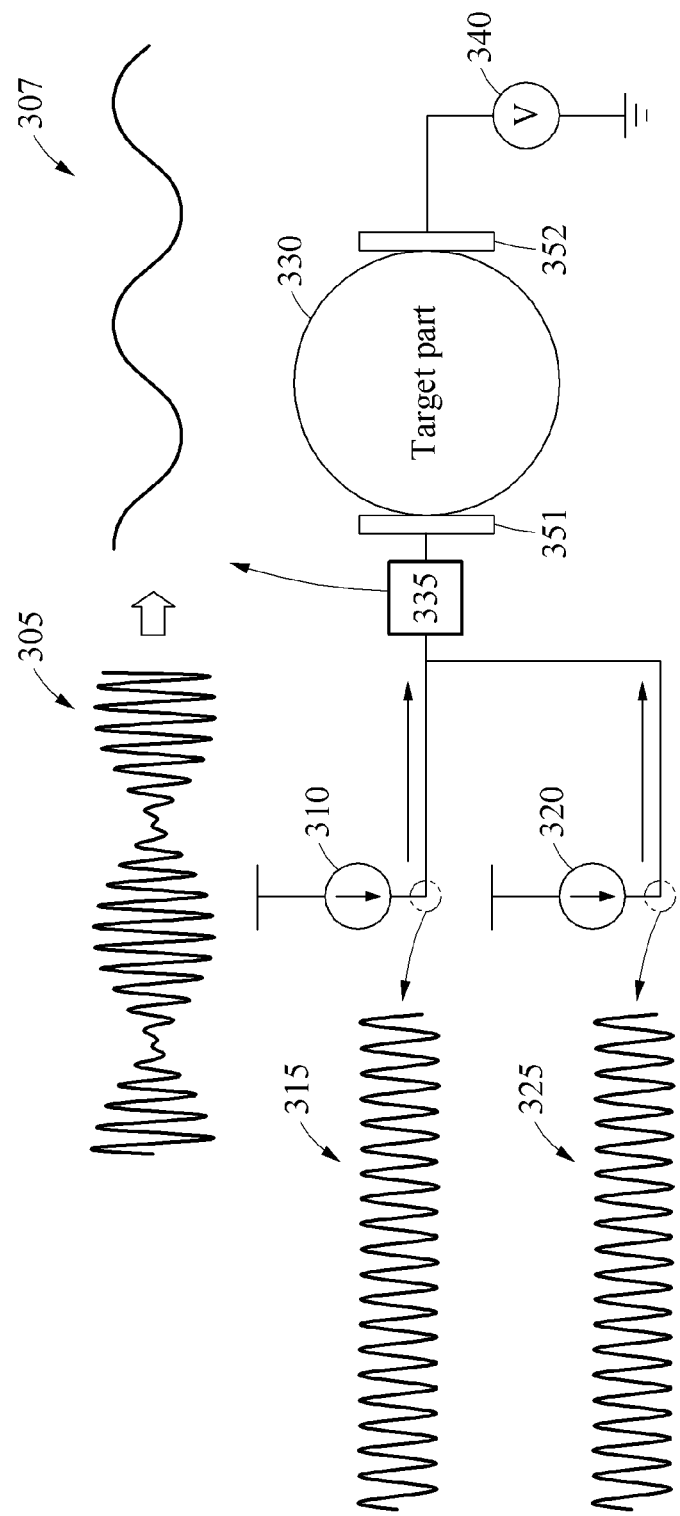
FIG. 3 illustrates an example of a process of generating a low-frequency signal using a beat phenomenon, in accordance with one or more embodiments.

FIG. 3 illustrates an example of a process of generating a low-frequency signal using a beat phenomenon, in accordance with one or more embodiments.

Referring to FIG. 3, a first high-frequency current generator 310 generates a first high-frequency current 315 and a second high-frequency current generator 320 generates a second high-frequency current 325. A beat current 305 is generated through a combination of the first high-frequency current 315 and the second high-frequency current 325. An envelope detector 335 generates a low-frequency current 307 by detecting an envelope from the beat current 305. The low-frequency current 307 is applied to an electrode 351. At this time, a voltage of a target part 330 is transferred to a biopotential measurer 340 through an electrode 352. As such, an impedance measuring apparatus generates the beat current 305 including a low-frequency component using the high-frequency current generators 310 and 320 without need to use a separate low-frequency current generator, and measures a voltage of the target part 330 based on the low-frequency current 307 corresponding to the low-frequency component of the beat current 305.

Figure 4:
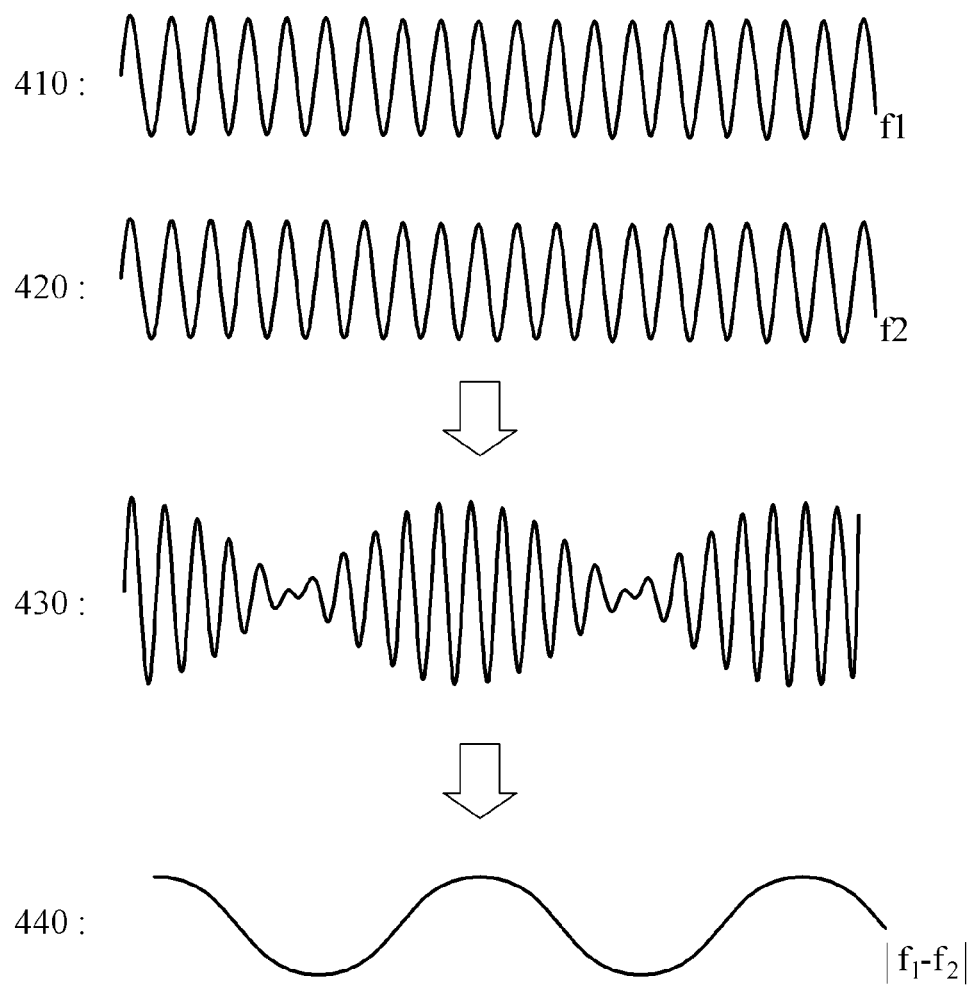
FIG. 4 illustrates an example of waveforms of signals in a process of generating a low-frequency signal, in accordance with one or more embodiments.

FIG. 4 illustrates an example of waveforms of signals in a process of generating a low-frequency signal, in accordance with one or more embodiments.

Referring to FIG. 4, a high-frequency signal 410 may correspond to the first high-frequency current 315 of FIG. 3 and a high-frequency signal 420 may correspond to the second high-frequency current 325 of FIG. 3. A frequency of the high-frequency signal 410 is denoted by f1 and a frequency of the high-frequency signal 420 is denoted by f2. Through a combination of the high-frequency signal 410 and the high-frequency signal 420, a beat signal 430 may be generated. By detecting an envelope of the beat signal 430, a low-frequency signal 440 is generated. A frequency of the low-frequency signal 440 is denoted by |f1−f2|. The low-frequency signal 440 may correspond to the low-frequency current 307 of FIG. 3. The impedance measuring apparatus generates high-frequency currents suitable for generating a desired low-frequency current. For example, the impedance measuring apparatus generates high-frequency currents having a frequency difference of f0 to generate a low-frequency current having a low-frequency of f0. The impedance measuring apparatus generates a beat current by combining the high-frequency currents having the frequency difference of f0 and uses an envelope of the beat current as a low-frequency current.

Figure 5:
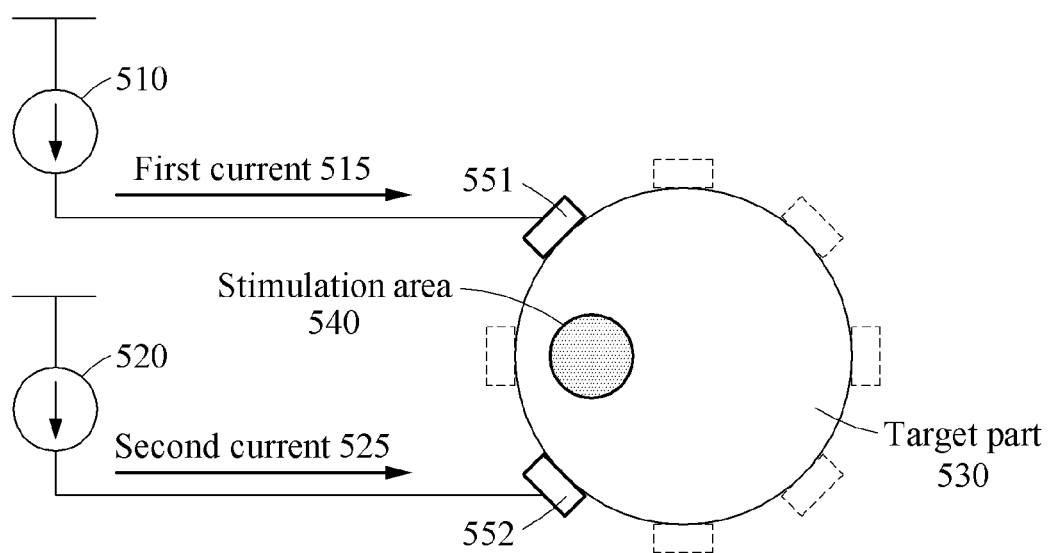
FIGS. 5 and 6 illustrate examples of a process of applying an electrical stimulus to a stimulation area, in accordance with one or more embodiments.
Figure 6:
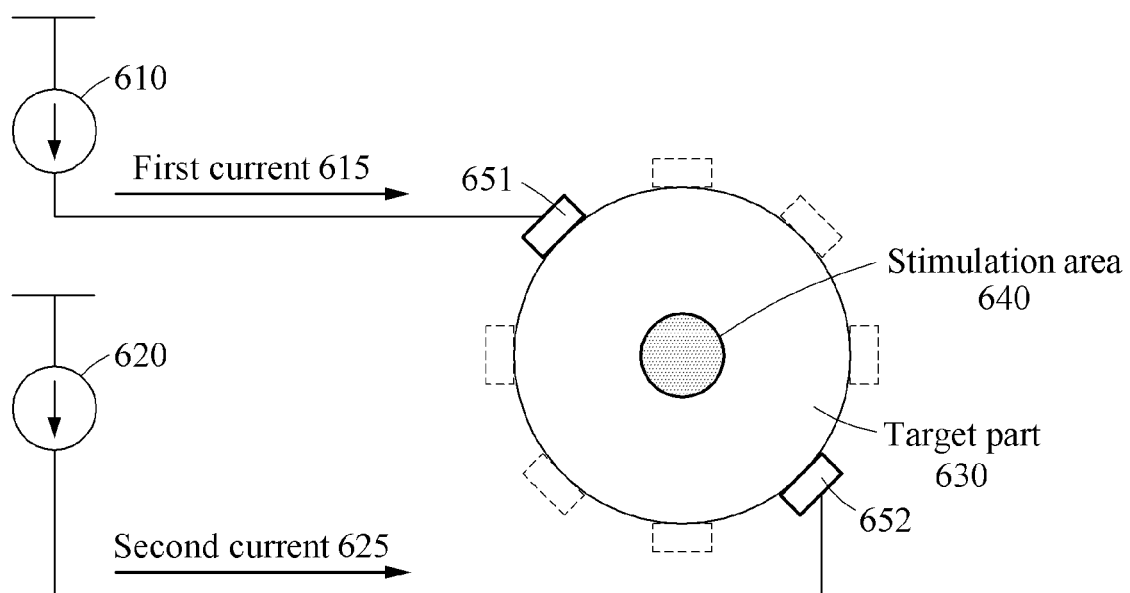

FIGS. 5 and 6 illustrate examples of a process of applying an electrical stimulus to a stimulation area in accordance with one or more embodiments.

Referring to FIG. 5, an impedance measuring apparatus applies an electrical stimulus to a stimulation area 540 in a target part 530 using a first current 515 and a second current 525. A high-frequency current generator 510 generates the first current 515 corresponding to a first high-frequency, and a high-frequency current generator 520 generates the second current 525 corresponding to a second high-frequency. The impedance measuring apparatus may selects electrode 551 and 552 from an electrode array to apply an electrical stimulus to the stimulation area 540 in the target part 530, and applies the first current 515 and the second current 525 to the selected electrodes 551 and 552.

When the first current 515 and the second current 525 are applied to the respective electrodes 551 and 552, the first current 515 and the second current 525 overlap in the stimulation area 540 such that a low-frequency electrical stimulus and a high-frequency electrical stimulus due to a beat phenomenon are induced to the stimulation area 540. The stimulation area 540 responds to the low-frequency electrical stimulus due to the beat phenomenon, but does not respond to the high-frequency electrical stimulus. Consequently, an effect like applying only the low-frequency electrical stimulus to the simulation area 540 is achieved. The low-frequency electrical stimulus corresponds to a difference between the first high-frequency and the second high-frequency. The impedance measuring apparatus selects the electrodes 551 and 552 by referencing a database built in advance. Additionally, the impedance measuring apparatus controls the high-frequency current generator 510 and the high-frequency current generator 520 such that the first current 515 and the second current 525 are generated at frequencies suitable for applying the electrical stimulus to the stimulation area 540.

Referring to FIG. 6, an impedance measuring apparatus applies an electrical stimulus to a stimulation area 640 in a target part 630 using a first current 615 and a second current 625. A position of the stimulation area 640 in FIG. 6 differs from a position of the stimulation area 540 in FIG. 5. The impedance measuring apparatus may select electrodes 651 and 652, which are in positions different from the positions of the electrodes 551 and 552 of FIG. 5 from an electrode array, to stimulate the stimulation area 640, which is different from the stimulation area 540. When the first current 615 and the second current 625 are applied to the electrodes 651 and 652, the first current 615 and the second current 625 overlap in the stimulation area 640 such that a low-frequency electrical stimulus and a high-frequency electrical stimulus due to a beat phenomenon are induced to the stimulation area 640. The stimulation area 640 responds to the low-frequency electrical stimulus due to the beat phenomenon, but does not respond to the high-frequency electrical stimulus. Consequently, an effect like applying only the low-frequency electrical stimulus to the simulation area 640 is achieved. The impedance measuring apparatus may select the electrodes 651 and 652 by referencing a database built in advance, or may control the high-frequency current generator 610 and the high-frequency current generator 620 such that the first current 615 and the second current 625 are generated at frequencies suitable for applying the electrical stimulus to the stimulation area 640.

As a non-limiting example, the target parts 530 as illustrated in FIGS. 5 and 630 as illustrated in FIG. 6 may correspond to nerve bundles, and the stimulation areas 540 as illustrated in FIGS. 5 and 640 as illustrated in FIG. 6 may correspond to at least one nerve in the nerve bundles. For example, the target parts 530 and 630 may correspond to sciatic nerves and the stimulation areas 540 and 640 may respectively correspond to a tibial nerve and a common peroneal nerve included in the sciatic nerves.

Figure 7:
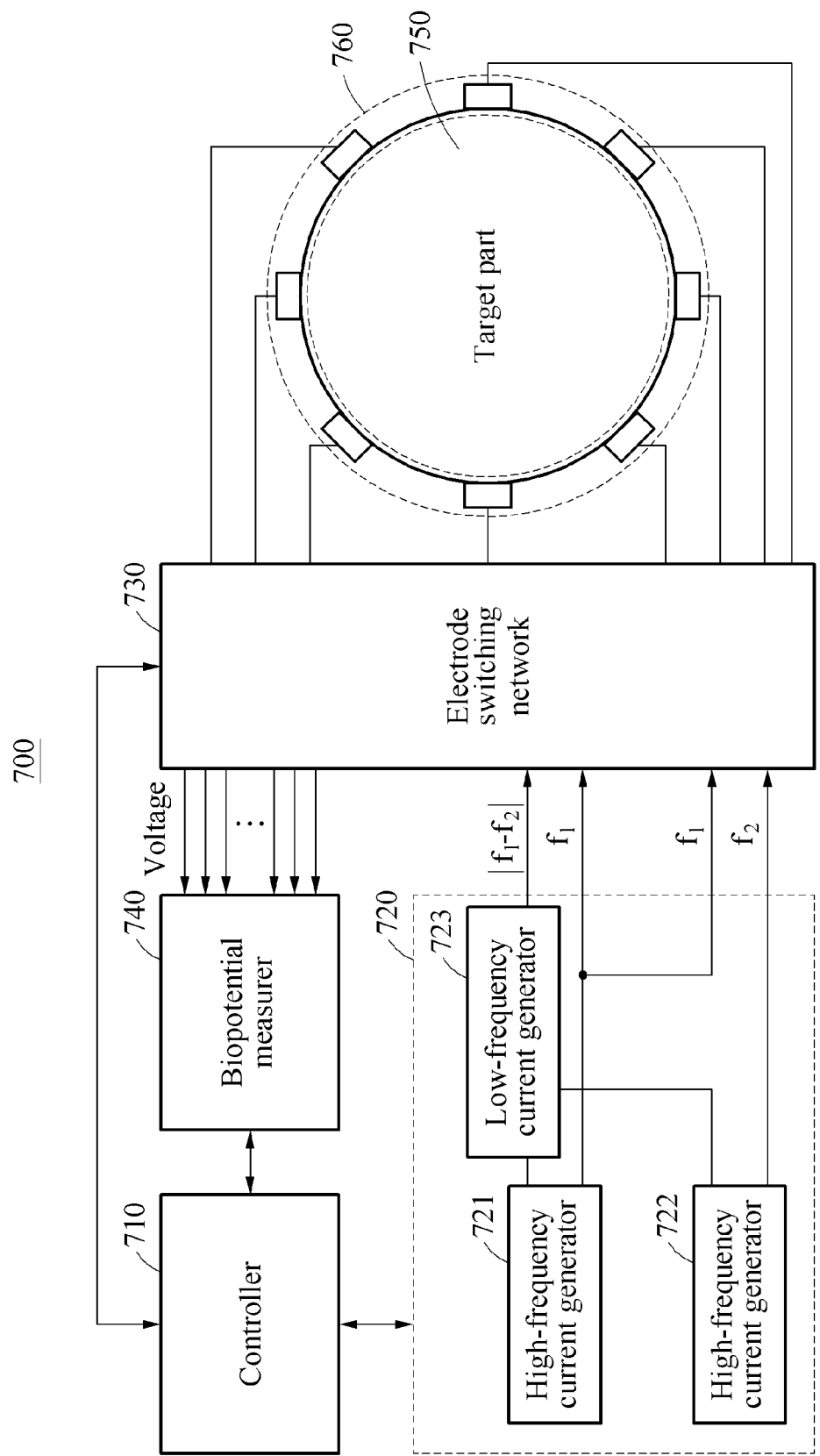
FIG. 7 illustrates an example of an impedance measuring apparatus, in accordance with one or more embodiments.

FIG. 7 illustrates an example of an impedance measuring apparatus in accordance with one or more embodiments.

Referring to FIG. 7, an impedance measuring apparatus 700 includes a controller 710, a current generating circuit 720, an electrode switching network 730, a biopotential measurer 740, and an electrode array 760. The impedance measuring apparatus 700 measures a bioimpedance of a target part 750 or applies an electrical stimulus to a stimulation area in the target part 750.

The current generating circuit 720 includes high-frequency current generators 721 and 722 and a low-frequency current generator 723. The high-frequency current generators 721 and 722 may generate currents based on a frequency corresponding to a command of the controller 710. For example, the high-frequency current generator 721 may generate a first current corresponding to a first high-frequency f1 under a control of the controller 710. The high-frequency current generator 722 may generate a second current corresponding to a second high-frequency f2 under a control of the controller 710. The low-frequency current generator 723 may generate a low-frequency current corresponding to a difference |f1−f2| between the first high-frequency f1 and the second high-frequency f2 based on the first current and the second current. The low-frequency current generator 723 may generate a beat current through a combination of the current of the first high-frequency f1 and the current of the second high-frequency f2, and generate the low-frequency current based on an envelope of the beat current.

The electrode array 760 includes electrodes contacting the target part 750. The electrodes are arranged at intervals to surround the target part 750. In an example, the target part 750 may correspond to a nerve bundle, and the electrodes of the electrode array 760 may be arranged to surround the nerve bundle corresponding to the target part 750.

The biopotential measurer 740 may measure a voltage applied to a target part based on a high-frequency current and a low-frequency current. For example, the biopotential measurer 740 measures a voltage applied to the target part 750 while a high-frequency current is applied to the target part 750 and measures a voltage applied to the target part 750 while a low-frequency current is applied to the target part 750. The controller 710 calculates an impedance of the target part 750 based on the voltage induced to the target part 750 by the high-frequency current and the low-frequency current. For example, the high-frequency current may correspond to at least one of the first current corresponding to the first high-frequency f1 and the second current corresponding to the second high-frequency f2, and the low-frequency current may correspond to an envelope of the beat current corresponding to the frequency difference |f1−f2|.

The electrode switching network 730 selectively connects at least one of the high-frequency current generator 721, the high-frequency current generator 722, the low-frequency current generator 723, and the biopotential measurer 740 to at least one of the electrodes of the electrode array 760 under the control of the controller 710.

For example, the electrode switching network 730 may connect the high-frequency current generator 721 and the low-frequency current generator 723 to the electrodes of the electrode array, so that a low-frequency current corresponding to a frequency of |f1−f2| and a first current corresponding to a high-frequency of f1 is applied to the target part 750 in the impedance measurement mode. Also, when the low-frequency current and the first current are applied to the target part 750, the electrode switching network 730 connects the biopotential measurer 740 to the electrodes of the electrode array 760. The electrode switching network 730 performs a switching operation such that a rotation of current electrodes and voltage electrodes is conducted. Although FIG. 7 illustrates that the first current corresponding to the high-frequency of f1 is provided in the impedance measurement mode, the second current corresponding to the high-frequency of f2 may also be provided instead of the first current corresponding to the high-frequency of f1.

When a stimulation area is selected from the target part 750 in a selective stimulation mode, the controller 710 may select electrodes corresponding to the stimulation area from the plurality of electrodes included in the electrode array 760. When the first current corresponding to the high-frequency of f1 and the second current corresponding to the high-frequency of f2 are applied to the selected electrodes, the first current and the second current overlap in the stimulation area such that a low-frequency electrical stimulus and a high-frequency electrical stimulus due to a beat phenomenon are induced to the stimulation area, and the stimulation area responds to the low-frequency electrical stimulus only. The electrode switching network 730 connects the high-frequency current generators 721 and 722 to the electrodes selected by the controller 710 such that the first current and the second current are applied to the selected electrodes. The controller 710 determines frequencies, for example, f1 and f2 by referencing a database or selecting electrodes corresponding to a stimulation area.

Figure 8:
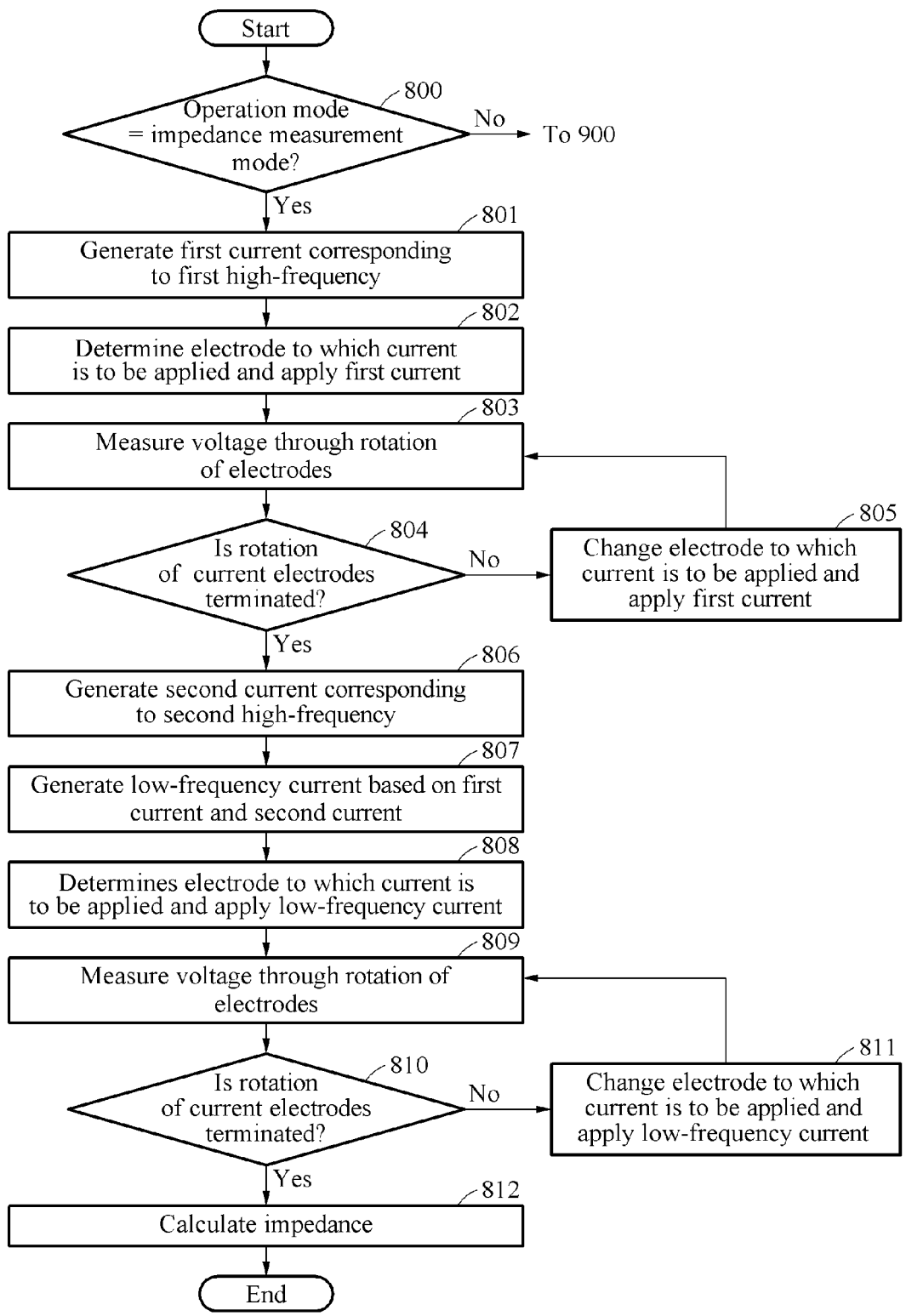
FIG. 8 is a flowchart illustrating an example of an impedance measurement process based on an impedance measurement mode, in accordance with one or more embodiments.

FIG. 8 is a flowchart illustrating an example of an impedance measurement process based on an impedance measurement mode. The operations in FIG. 8 may be performed in the sequence and manner as shown, although the order of some operations may be changed or some of the operations omitted without departing from the spirit and scope of the illustrative examples described. Many of the operations shown in FIG. 8 may be performed in parallel or concurrently. One or more blocks of FIG. 8, and combinations of the blocks, can be implemented by special purpose hardware-based computer that perform the specified functions, or combinations of special purpose hardware and computer instructions. In addition to the description of FIG. 8 below, the descriptions of FIGS. 1-7 are also applicable to FIG. 8, and are incorporated herein by reference. Thus, the above description may not be repeated here.

Figure 9:
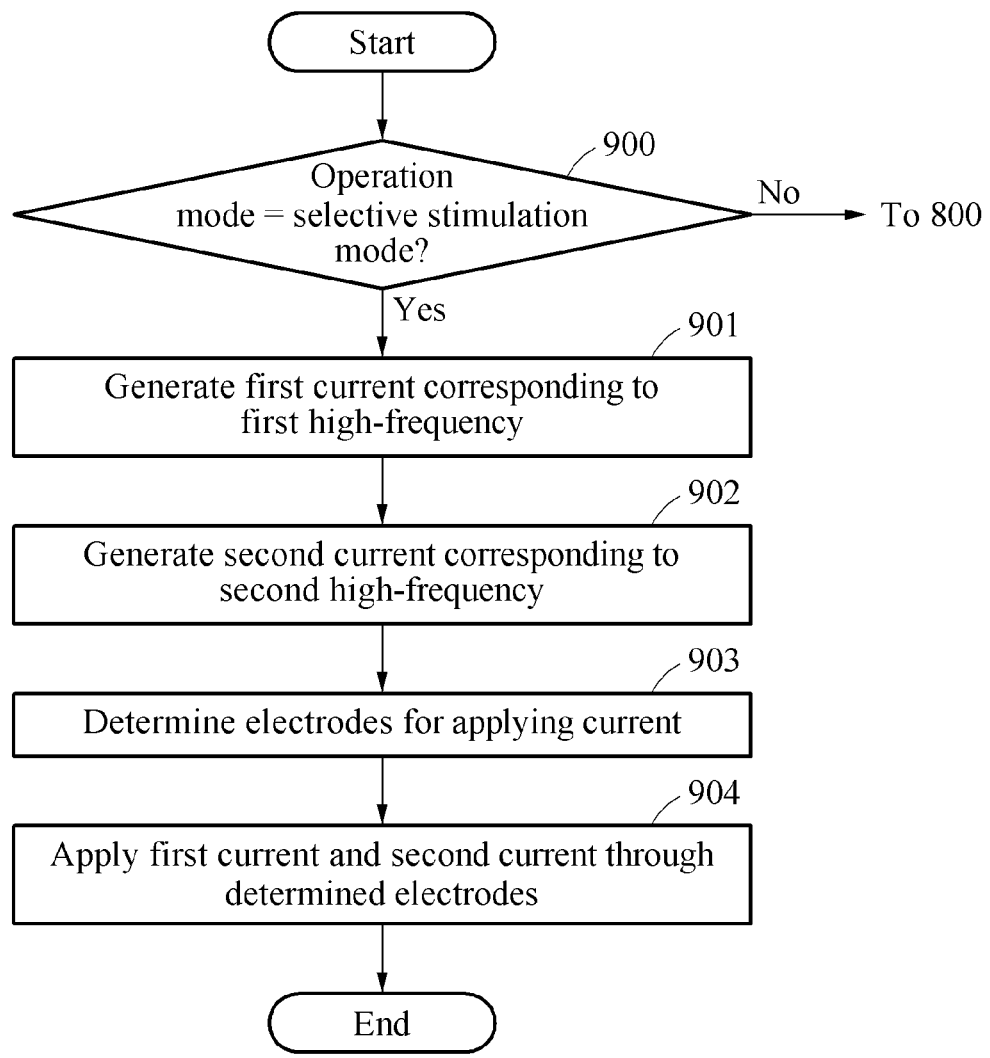
FIG. 9 is a flowchart illustrating a stimulation process based on a selective stimulation mode, in accordance with one or more embodiments.

Referring to FIG. 8, in operation 800, an impedance measuring apparatus determines whether an operation mode corresponds to an impedance measurement mode. When the operation mode corresponds to the impedance measurement mode, operation 801 is performed. When the operation mode does not correspond to the impedance measurement mode, operation 900 as illustrated in FIG. 9 is performed. Operation 900 will be described with reference to FIG. 9.

The impedance measuring apparatus generates a first current corresponding to a first high-frequency in operation 801. The impedance measuring apparatus determines an electrode to which a current is to be applied, and applies the first current to the electrode in operation 802. The impedance measuring apparatus measures a voltage through a rotation of electrodes in operation 803. For example, when the first current is applied to a first electrode, the impedance measuring apparatus may measure a voltage through a rotation of electrodes other than the first electrode in an electrode array.

In operation 804, the impedance measuring apparatus determines whether a rotation of current electrodes is terminated. When the rotation of current electrodes is not terminated, the impedance measuring apparatus changes an electrode to which a current is to be applied and applies the first current to the changed electrode in operation 805. Also, the impedance measuring apparatus may perform operations 803 and 804 again. Through this, such current application and voltage measurement based on the first current may be performed on all electrodes included in the electrode array.

When the rotation of current electrodes is terminated, the impedance measuring apparatus generates a second current corresponding to a second high-frequency in operation 806 and generates a low-frequency current based on a beat phenomenon of the first current and the second current in operation 807. The impedance measuring apparatus selects the first high-frequency and the second high-frequency such that a low-frequency current corresponding to a desired low-frequency is generated.

Operations 808 through 811 may correspond to operations 802 through 805. The impedance measuring apparatus determines an electrode to which a current is to be applied and applies the low-frequency current to the electrode in operation 808. The impedance measuring apparatus measures a voltage through a rotation of electrodes in operation 809. The impedance measuring apparatus determines whether a rotation of current electrodes is terminated in operation 810. When the rotation of current electrodes is not terminated, the impedance measuring apparatus changes an electrode to which a current is to be applied and applies the low-frequency current to the changed electrode in operation 811. Additionally, the impedance measuring apparatus may perform operations 809 and 810 again. Through this, such current application and voltage measurement based on the low-frequency current may be performed on all electrodes included in the electrode array.

When the rotation of current electrodes is terminated, the impedance measuring apparatus calculates an impedance in operation 812. The impedance measuring apparatus calculates a bioimpedance of the target part based on values of the measured voltage, the low-frequency current (an envelope of the beat current), and the first current. The description made with reference to FIGS. 1 through 7 is also applicable to the impedance measurement process.

FIG. 9 is a flowchart illustrating a stimulation process based on a selective stimulation mode. The operations in FIG. 9 may be performed in the sequence and manner as shown, although the order of some operations may be changed or some of the operations omitted without departing from the spirit and scope of the illustrative examples described. Many of the operations shown in FIG. 9 may be performed in parallel or concurrently. One or more blocks of FIG. 9, and combinations of the blocks, can be implemented by special purpose hardware-based computer that perform the specified functions, or combinations of special purpose hardware and computer instructions. In addition to the description of FIG. 9 below, the descriptions of FIGS. 1-8 are also applicable to FIG. 9, and are incorporated herein by reference. Thus, the above description may not be repeated here.

Referring to FIG. 9, in operation 900, an impedance measuring apparatus determines whether an operation mode corresponds to a selective stimulation mode. When the operation mode corresponds to the selective stimulation mode, operation 901 is performed. When the operation mode does not correspond to the selective stimulation mode, operation 800 as illustrated in FIG. 8 is performed. The impedance measuring apparatus generates a first current corresponding to a first high-frequency in operation 901. The impedance measuring apparatus generates a second current corresponding to a second high-frequency in operation 902. The impedance measuring apparatus determines electrodes for applying a current in operation 903. The impedance measuring apparatus applies the first current and the second current through the determined electrodes in operation 904. When the first current and the second current are applied to the determined electrodes, the first current and the second current overlap in a stimulation area such that a low-frequency electrical stimulus and a high-frequency electrical stimulus due to a beat phenomenon are induced to the stimulation area, and the stimulation area responds to the low-frequency electrical stimulus only. The description made with reference to FIGS. 1 through 7 is also applicable to the stimulation process.

The impedance measuring apparatus 110, the impedance measuring apparatus 700, the controller 710, the high frequency current generator 721, the high frequency current generator 722, the biopotential measurer 740, the low-frequency current generator 723, the electrode switching network 730, and other apparatuses, devices, and other components described herein with regard to FIGS. 1-9 are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated and discussed with respect to FIGS. 1-9 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations performed by the hardware components and the methods as described above. In one example, the instructions or software include machine code that is directly executed by the one or more processors or computers, such as machine code produced by a compiler. In another example, the instructions or software include higher-level code that is executed by the one or more processors or computers using an interpreter. The instructions or software may be written using any programming language based on the block diagrams and the flow charts illustrated in the drawings and the corresponding descriptions in the specification, which disclose algorithms for performing the operations performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-Res as non-limiting, blue-ray or optical disk storage examples, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An electronic device comprising:
 a plurality of electrodes configured to contact a body part;
 a first high-frequency current generator configured to generate a first high-frequency current;
 a second high-frequency current generator configured to generate a second high-frequency current;
 a low-frequency current generator configured to receive the first high-frequency current and the second high-frequency current and generate a current of a low-frequency corresponding to a difference between a first high-frequency of the first high-frequency current and a second high-frequency of the second high-frequency current; and
 a controller configured to select electrodes to which the first high-frequency current and the second high-frequency current are to be applied, from among the plurality of electrodes.

2. The electronic device of claim 1, wherein the first high-frequency and the second high-frequency range 20 to 200 kilohertz (KHz).

3. The electronic device of claim 1, wherein the low-frequency ranges from 5 to 30 hertz (Hz).

4. The electronic device of claim 1, wherein the total volume of the first high-frequency current generator, the second high-frequency current generator, and the low-frequency current generator is less than 1 cubic centimeter (cm3).

5. The electronic device of claim 1, wherein the first high-frequency current generator and the second high-frequency current generator are configured as a chip, and the area of the chip is less than 25 square millimeters (mm2).

6. The electronic device of claim 1, wherein a mode in which the controller applies the first high-frequency current and the second high-frequency current to the selected electrodes is a stimulation mode, and
 the controller has a measurement mode for applying the low-frequency current.

7. The electronic device of claim 1, wherein the controller is further configured to select the electrodes to which the generated low-frequency current is to be applied, from among the plurality of electrodes.

8. The electronic device of claim 7, wherein the controller is further configured to select one or more of the generated low-frequency current, the first high-frequency current, and the second high-frequency current to the selected electrodes based on an operating mode of the electronic device.

9. The electronic device of claim 7, further comprising a biopotenial measurer configured to measure a voltage applied to the body part based on the generated low-frequency current and one of the first high-frequency current and the second high-frequency current being applied to the selected electrodes.

10. The electronic device of claim 7, wherein the controller applies the first high-frequency current and the second high-frequency current to the selected electrodes in a stimulation mode, and
 wherein the controller applies the low-frequency current and one of the first high-frequency current and the second high-frequency current to the selected electrodes in a measurement mode.

* * * * *